United States Patent [19]

Wang

[11] Patent Number: 4,553,936
[45] Date of Patent: Nov. 19, 1985

[54] DENTAL IMPRESSION TRAY AND METHOD OF USE

[75] Inventor: Wu-Lan Wang, Milford, Del.

[73] Assignee: Dentsply Research & Development Corp., Milford, Del.

[21] Appl. No.: 636,175

[22] Filed: Jul. 31, 1984

[51] Int. Cl.$^4$ ............................................. A61O 9/00
[52] U.S. Cl. ...................................... 433/37; 433/229
[58] Field of Search ................................. 433/229, 37

[56] References Cited

U.S. PATENT DOCUMENTS

| | | | |
|---|---|---|---|
| 1,084,017 | 1/1914 | Lautenburg | 433/37 |
| 4,449,928 | 5/1984 | Von Weissenfluh | 433/229 |

Primary Examiner—Robert Peshock
Attorney, Agent, or Firm—Edward J. Hanson, Jr.; C. Hercus Just

[57] ABSTRACT

A dental impression tray and method of using it to form in a light-polymerizable impression material an impression of a portion of dental anatomy in an oral cavity, the tray being formed of transparent substantially rigid material, preferably clear plastic, and molded into a channel-like shape defined by walls capable of having visible actinic light applied to the walls of the tray for transmission along and through the walls, and substantially all the exterior surfaces of the walls having light reflecting metal foil or the equivalent applied thereto for the dual purpose of preventing unintentional light exposure to material in the tray and subsequently providing a light reflecting surface operable to reflect light into the impression material. The tray also may be loaded with polymerizable impression material and have a cover sheet sealed to the rim of the tray and thereby become a package conveniently ready for use simply by peeling the cover sheet from the rim of the tray to expose the impression material for immediate impression onto dental anatomy of which a model is to be made.

15 Claims, 7 Drawing Figures

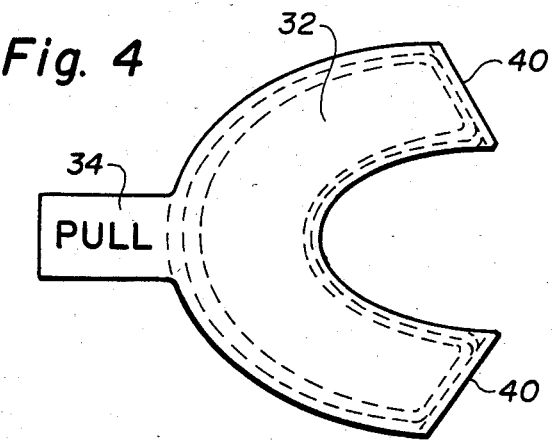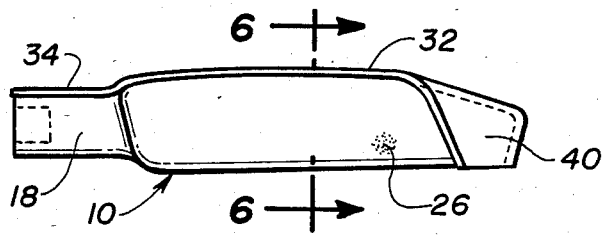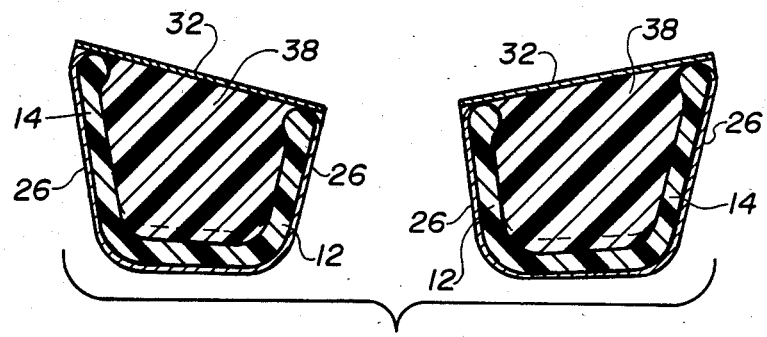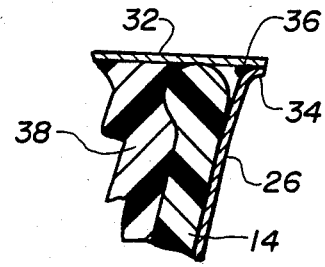

DENTAL IMPRESSION TRAY AND METHOD OF USE

BACKGROUND OF THE INVENTION

This invention pertains to a dental impression tray and a method of using the same to effect maximum curing by polymerization of impression material to form a negative impression of at least a part of dental anatomy in an oral cavity, the polymerization being effected by visible actinic light rays applied to the tray and impression material therein while the tray and said material are held firmly pressed against the dental anatomy which is to be reproduced in the form of a model or otherwise.

In general, for many years, it has been common practice in dentistry to form a model or cast of dental anatomy in the oral cavity of a patient by utilizing a suitable size and shape of a dental impression tray into which a predetermined amount of settable impression material is placed for manual impressment against the anatomy, such as a full or partial gum, with or without teeth. Normally, an appreciable amount of time is required to effect, by currently used activators and otherwise, suitable curing of presently available impression material into an elastomeric form having permanent memory. This technique necessarily monopolizes the full time of a denist or assiatant for the required period of curing time and during which, no other activities can be undertaken by the dentist or assistant.

Dental impression trays have been used for many years to contain pastes, for example, during the taking of impression of oral tissues or dental anatomy. Usually these trays are of metal and exist in a variety of shapes and sizes suitable for various situations. In recent years plastics have been substituted for metal, particularly for single use so as to be disposable. Some of these trays have been fitted with coolant systems for hardening pastes into gels but, in most instances, the viscous pastes are converted to elastic or rubbery condition by a reaction initiated by the mixing of two components immediately before the material is placed in the tray.

One recurrent problem with presently used dental impression trays is that the gelatinous or elastic material requires an integral non-distorting foundation. Adhesion of the elastomers to trays has been achieved by either perforating the trays or the use of adhesives.

Another problem with existing impression trays and taking impressions is that a significant amount of the mouth area is being covered by a large object for a long period of time—up to fifteen minutes, for example. The natural human reflex action in this situation is to gag, resulting in changing the contours of some of the tissue and musculature which was to be reproduced while static. Also, with the passage of several minutes times, salivation occurs from glands located near the impression area and these fluids affect the quality of impression reproduction.

A recent dental development has occurred in the area of restoratives and sealants where actinic radiation has been used in conjunction with phototsensitive accelerators to initiate prompt and rapid polymerization precisely when the dentist is ready with the patient. Heretofore, however, radiation curing has not been applied to elastomers, to large areas, or to materials needing to be confined in a radiation-conducting vehicle.

Particularly for purposes of shortening the time required to transform such impression material into a practical permanent elastomeric form having memory, and to avoid mixing a plurality of ingredients to form the material, the present invention has been conceived and reduced to practice by devising a novel type of impression tray with which harmless visible actinic light is used to effect curing the material by polymerizing novel impression material comprising the subject matter of one or more companion patent applications filed on even date herewith and assigned to the same assignee as the instant invention.

SUMMARY OF THE INVENTION

It is the principal object of the invention to provide a dental impression tray formed from transparent material which may have visible actinic light applied thereto for a relatively short period of time for the purposes of photo-curing polymerizable impression material in said tray to convert the same into a mold having a permanent elastomeric form which has memory.

Another object of the invention is to provide a dental impression tray of the above-mentioned type having walls defining a recess which contains a predetermined amount of impression material of the type which is polymerizable within a relatively short period of time, such as on the order of two or three minutes or less, into a mold having a permanent elastomeric molding cavity which has memory, and to enhance the polymerization of the impression material by visible actinic light, means for reflecting the light into the material are disposed preferably on all exterior surfaces of the walls of the tray.

Still another object of the invention ancillary to the foregoing object is to provide said reflecting means in the form of bright reflective metal foil applied against all exterior surfaces of the walls of the tray, or a bright metal reflective plating may be applied to all said exterior surfaces of said walls of the tray either by a sputtering technique or electronic plating process, for example.

A further object of the invention is to provide a dental impression tray in the form of a package including a tray of the type referred to hereinabove which is substantially filled with polymerizable impression material and an opaque cover sheet is applied peelably over the impression material and sealed at the edged thereof by cement or otherwise at least to the upper edges of the walls of said tray or the reflective foil or plating applied to the exterior walls of said tray, whereby the cover sheet may be removed immediately prior to use and the impression material applied to the anatomy desired.

Details of the foregoing objects and of the invention as well as other objects are set forth below in the following specification and illustrated in the accompanying drawings comprising a part thereof.

DESCRIPTION OF THE DRAWINGS

FIG. 4 is a top plan view of an impression tray of the type shown in FIG. 1 which has been filled with impression material and is covered by a removable and opaque cover sheet sealed with respect to an opaque outer layer or coating to prevent access of visible light rays to the material in the tray.

FIG. 5 is a side elevation of the loaded impression tray shown in FIG. 4.

FIG. 6 is a vertical sectional view of the loaded tray as seen on the line 6—6 of FIG. 5 and being illustrated on a larger scale than in FIG. 5.

FIG. 7 is a fragmentary vertical sectional view of a further embodiment of the invention directed to sealing means for the opaque cover for the tray.

DETAILED DESCRIPTION OF THE PREFERRED EMBODIMENT OF THE INVENTION

Figure 1:
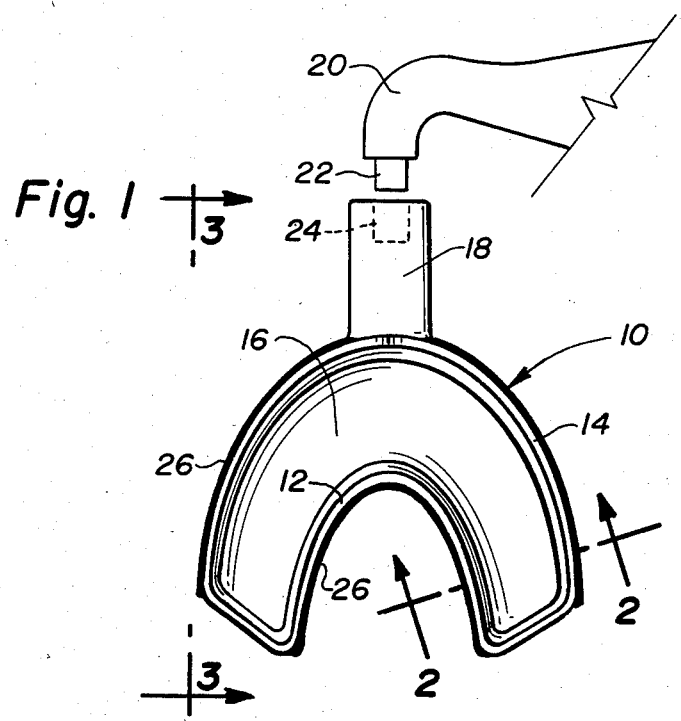
FIG. 1 is a fragmentary and slightly exploded view of an impression tray embodying the principals of the present invention and shown in process of having a source of light applied thereto, the light source being fragmentarily illustrated.

The present invention has several important aspects, the first comprising an impression tray made of transparent material molded into a rigid tray configuration similar in shape to conventional metallic impression trays, the transparency being utilized to transmit actinic light preferably into all walls of the tray while the tray contains light-polymerizable impression material which is held in contact with a desired portion of dental anatomy within an oral cavity. The preferred impression material is novel and comprises the subject matter of at least one companion application. To enhance and maximize the polymerization of the material in the shortest possible time, light reflective means are applied preferably to all of the outer wall surfaces of the tray in order that light rays will be reflected back into the body of the impression material from the reflecting means.

A second aspect of the invention comprises utilizing light reflecting means on the outer walls of the tray which are of an opaque nature and, in conjunction with a cover sheet of opaque material which extends across the material within the tray and is sealed at the peripheral thereof, for example, to the upper edges of the wall of the tray or the upper edges of opaque light reflecting means on the outer surfaces of the walls of the tray, such a sealed impression tray comprises a convenient and efficient package for impression material which is rendered ready for instant use simply by peelably removing the cover sheet from the loaded tray, such, for example, as immediately prior to applying the tray and the impression material therein to a portion of dental anatomy.

As indicated above, utilizing conventional opaque and metallic impression trays with conventional and presently used impression material usually requires a minimum of 10 minutes and generally more, such as, up to a limit of about 15 or more minutes. The tray and the conventional material in it must be held against the dental anatomy either by a dentist or an assistant for the stated period of time without the possibility of employing any of that time for other purposes. Accordingly, one of the principal objectives of the present invention as stated above is to greatly shorten the period of time required to from a permanent elastomeric mold of the improved impression material referred to above and described in detail below, said mold having memory and being an accurate negative reproduction of the shape of the dental anatomy against which it is applied in order, for example, that a cast or model of suitable material such as certain gypsum products, may be formed into the fabrication of dental restorations of various kinds.

Another objective of the invention is to shorten the required time for polymerization of the impression material by intesifying the same by reflecting actinic light from the exterior wall surfaces of the tray directly back into the mass of the impression material, rather than rely solely upon the actinic rays as applied to certain areas of the transparent tray and the passage of the rays through the body of the walls of the tray.

Another advantage of the present invention is the fact that in utilizing conventional impression material, a mixture of two or more components is required to place the material in workable condition, whereas the present invention contemplates the use of a pre-mixed material which is supplied in the tray as sold, such as referred to above, or in suitable opaque packages, syringes, or the like.

Figure 3:
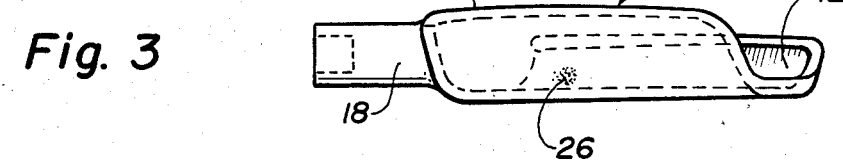
FIG. 3 is a side elevation of the tray shown in FIG. 1 as seen from the left-hand side thereof as viewed in said figure.
Figure 2:
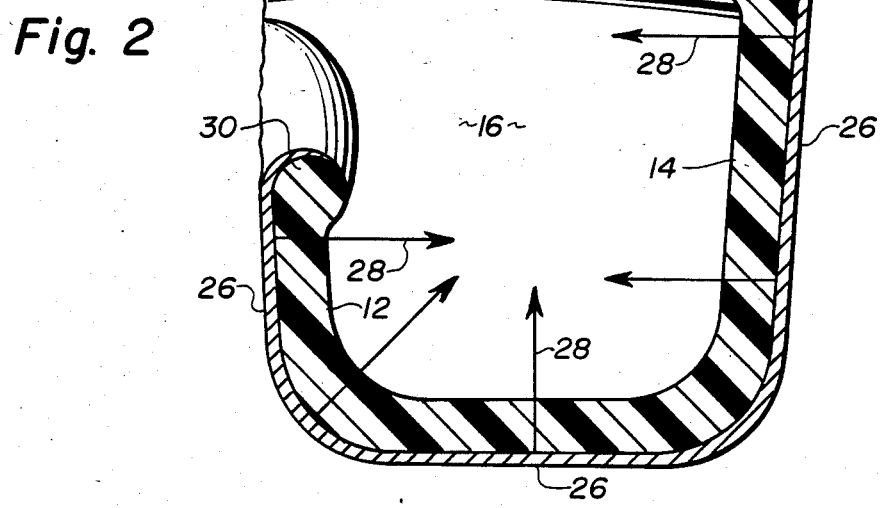
FIG. 2 is an enlarged, fragmentary vertical sectional view of a portion of the impression tray shown in FIG. 1 as seen on the line 2—2 thereof.

Referring to the drawing and particularly FIGS. 1–3, it is to be understood that the substantially U-shaped transparent dental tray is an exemplary shape and is shown in top plan view. It comprises an inner sidewall 12 and an outer sidewall 14, said walls forming therebetween a recess or channel 16 within which impression material of the type referred to above and described in detail hereinafter is placed for application to dental anatomy. While it is within the realm of the present invention that the transparent tray 10 can be formed of clear glass, for example, especially for purposes of rapid and inexpensive production, it is preferred that the tray shall be molded from suitable plastic material of a substantially rigid nature, such as a suitable polycarbonate, or methylmethacrylate, to mention only a few which can be utilized.

As seen from FIG. 1, actinic light receiving means is illustrated in the form of a projection 18 which is integral with the outer wall 14 of tray 10 and is adapted to have actinic rays applied thereto from a source comprising harmless visible light discharged from the tip 20 of a light source handpiece, such as the type shown, described and claimed in prior U.S. Pat. No. 4,385,344, to Gonser, dated May 24, 1983, and assigned to the assignee of the present invention. If desired, the terminal end 22 of the handpiece may comprise optical fibers and the outer end of the projection 18 may be provided with a socket 24 into which the terminal end 22 may be inserted. It has been found that when actinic light of the type developed by the instrument comprising the subject matter of the aforementioned prior U.S. Patent, the light rays are conducted to all areas of the walls 12 and 14 of the tray 10 formed, for example, of the materials referred to above, in a substantially even manner.

For purposes of enhancing and maximizing the polymerization of the impression material disposed in the recess or channel 16 in the shortest possible time, it is preferred in accordance with the principals of the present invention, that the outer surfaces of all wall portions of the tray 10 have applied thereto an opaque light reflecting means 26 which, for example, may comprise bright aluminum foil or other bright metal foil or, if desired, a coating or plating of suitable bright metal or other bright substance such as barium sulphate. Such metallic plating may be effected either electrically or by a sputtering process of known type. Also, it is possible to apply a metal foil to the outer surfaces of the tray by disposing a suitable shape of metal foil within the female mold of an injection type mold which, when the male mold member is affixed to the female mold and plastic material is injected into the cavity, the metal foil will be closely bonded to the outer surfaces of the molded tray, whereby a laminated wall is produced.

Referring to FIG. 2, it will be seen that the enlarged cross sectional illustration includes the foil layer or other type of light reflecting means 26 which is bonded to the exterior surfaces of the sidewalls and bottom of the tray 10 or applied thereto in any of the methods referred to above. The exemplary arrows 28 illustrate, somewhat diagramatically, the reflection of actinic light rays from the reflecting means 26 into the body of impression material and disposed within the dental tray between the sidewalls thereof. Also referring to FIG. 2, it will be seen that the upper edges of the sidewalls 12 and 14 terminate in longitudinal enlargements 30 which form somewhat of an undercut feature serving to retain the impression material within the channel 16, and especially to hold the polymerized mold-forming material within the tray, such as when it is being withdrawn from the anatomy with which it has been in engagement and for other purposes of maintaining the elastomeric mold connected to the tray.

Hereinabove, reference is made to the impression tray 10 also serving as a package in which predetermined quantities of impression material may be mounted and stored until ready for use. Due to the fact that the preferred impression material is light-sensitive and exposure to ambient light of most types will effect polymerization of the impression material, whether desired or not, the light reflecting material 26 applied to the outer walls of the impression tray must be of an opaque type. To maintain a predetermined quantity of impression material within the tray without being subject to ambient light, a cover sheet 32, stamped, for example, from sheet foil or opaque plastic material, is applied to the upper edges of the sidewalls 12 and 14, such as shown in exemplary manner in FIG. 6, for example, or in the event that the upper edges of the light reflecting material 26 extend somewhat across the upper edges of the sidewalls as shown in FIG. 2, the periphery of the cover sheet 32 may be suitably bonded by cement or otherwise, either directly to the upper edges of the light reflecting means 26 or directly to the upper edges of the sidewalls 12 and 14. Preferably, one end of the cover sheet 32 is provided with a pull tab 34 or the equivalent to facilitate removal of the same from the top of the tray 10 when it is to be inserted into the oral cavity for purposes of making an impression of a part of the anatomy therein.

Referring to FIG. 7, a further embodiment of connecting the cover sheet 32 to the tray is illustrated. In said figure, it will be seen that the upper edge of the light reflecting foil 26 or other type of reflecting material is provided with a terminal flange 34 which, preferably, extends laterally outward and the peripheral edge of the cover sheet 32 is coextensive with the same so that either by means of a line of cement 36 or by appropriate fusing or the like, all edges of the cover sheet 32 are securely bonded or afixed to the upper edges of the light reflecting material 36 so as to prevent the entrance of ambient light of any kind to the impression material 38 contained within the tray. It also will be seen from FIG. 5 that the outer ends 40 of the cover sheet 32 will extend downwardly so as to cover the open ends of the U-shaped channel 16 as shown in FIG. 1 and the peripheries of said outer ends 40 will be sealed relative to the terminal ends of the curved channel 16.

Particularly for purposes of simplifying the illustration of the present invention, only a single shape of impression tray has been illustrated, this being in the form of an arch or substantially U-shaped. While in general, such shape is one that is very commonly used in the practice of dental restoration, it is to be understood that many different forms and shapes of impression trays find use especially in special situations, such additional shapes being of well known nature and detailed illustration or reference thereto is not believed to be necessary. Suffice it to say that the illustrated shape basically is representative of substantially all useful shapes to which the present invention can be applied as long as the general purposes of the invention are present in the selected shapes.

While details of the preferred type of polymerizable impression material comprise the subject matter of one or more companion application which are filed on even dates herewith and identified as 1531 and 1534, and for purposes of furnishing at least one example of the practicality of the present invention a formulation of polymerizable impression material suitable for use with the novel impression tray principally described above and claimed herein, the following is set forth:

A prepolymer is prepared having the following composition:
Polypropylene glycol having a molecular weight of 4600 (Pluracol 628, BASF Wyandotte Corporation): 967.5 g
4,4' diphenylmethane diisocynate (Modur M): 65.6 g
Dibutyltin dilaureate: 0.5165 g The procedure for preparing the prepolymer was as follows;

The polypropylene glycol was dried to less than 300 ppm water.

The diisocyanate was adjusted to a temperature of 50° C. and charged to a clean, dry reactor equipped with an agitator, temperature control and temperature monitoring device. Once the isocyanate addition was complete, it was blanketed with nitrogen and the temperature was raised to 70° C. with agitation. The dibutyltin dilaureate was added to the reactor. Then the polyol was added to the reactor gradually while mixing thoroughly under the nitrogen blanket and the temperature was kept at 70°±3° C.

After all of the polyol was added, the mixture was kept at 75° C. to 80° C. for three hours. Then a sample was taken for excess free NCO analysis. Hydroxyethyl methacrylate (HEMA) was added at the same conditions as above to consume any remaining NCO. The mixture was then adjusted to about 80° C. and maintained at this temperature for another 3 hours. The mixture was then discharged into a container and is hereafter referred to as Product 1.

The polymerizable impression material was then formulated by mixing the following formulation at ambient conditions.

Product 1: 100 parts by weight
Camphoroquinone: 0.15 parts by weight
Methyl diethanol amine (MDEA): 0.5 parts by weight The principles of the present invention were then tested by grinding a portion out of one end of a glass rod of about 8 mm diameter for about ¾″ to provide a shallow recess into which a sample amount of the polymerizable impression composition was placed. A piece of bright aluminum foil was extended around the surface of the glass rod below the prepared surface and the composition upon it. Visible actinic light was applied to the opposite end of the glass rod and the light rays were transmitted to the prepared surface and reflected into the composition by the foil underlay. It was visually observed with the unaided eye and using hand manipulation, that the composition cured readily to an elastomer have permanent memory.

The novel impression tray and method of using the same described hereinabove comprises an advantageous advance in dental technology especially in the preparation of dental restorations. As has been indicated above, one of the principal advantages of the present invention comprises the substantial saving in time to convert a flowable or viscous impression material into a permanent elastomeric mold configuration having memory and suitable for making accurate reproductions of anatomical items in the oral cavity for use in the fabrication of dental restorations. The preferred novel polymerizable impression preferably is of a premixed nature and made available to a dental operatory or laboratory, whereby mixing of two or more ingredients is not necessary as has been required herebefore.

Effecting the conversion of the conventional flowable material into a permanent elastomeric mold requires a minimum of 8 to 10 minutes and frequently as much as 15 minutes or more, whereas with the present invention, the time for effecting polymerization of the preferred premixed impression material referred to hereinabove can be achieved in as little as 1 or 2 minutes and a maximum of 3 minutes, depending upon the strength of the visible actinic light applied to the material from the walls of the tray and especially as said light is reflected from the reflecting means on the exterior surfaces of the tray directly into the body or mass of the impression material. Further, the perferred visible actinic light which is to be employed in conjunction with the present invention is within the range of 360 to 600 nanometers and this has been found to be highly effective to polymerize the starting material into an elastomeric mold form having permanent memory.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. For use with dental impression material capable of being polymerized by exposure to actinic light, a dental impression tray curved sufficiently to receive at least a partial arch-shaped group of teeth and is channel-shaped in cross-section and wider than the teeth to be received therein, said tray being formed from relatively rigid material capable of transmitting actinic light and having a recess adapted to hold a predetermined amount of said impression material for forming the impression of opposite surfaces of said teeth thereinto, light-receiving means integral with said tray and adapted to receive and transmit light from said light-receiving means to dental impression material held in said recess to effect polymerization thereof to a degree that it has a permanent elastomeric form.

2. The impression tray according to claim 1 wherein said tray also comprises light-reflecting means thereon adapted to reflect light from said light-reflecting means into impression material within said recess.

3. The impression tray according to claim 2 in which said light-reflecting means comprises a thin layer of reflective metal.

4. The impression tray according to claim 3 in which said reflective metal is metal foil adhered to said external wall surfaces of said tray.

5. The impression tray according to claim 1 in which said recess is channel-like and said relatively rigid material is a clear transparent plastic capable of readily transmitting actinic light rays.

6. The impression tray according to claim 5 in which said light receiving means comprises a portion of the outer surface of the wall of said tray adapted and arranged to be contacted by a light-generating source.

7. The impression tray according to claim 6 further characterized by said portion of the wall of said tray comprising a projection extending a predetermined distance from an outer wall of said tray.

8. The impression tray according to claim 1 comprising opaque outer walls and further including therein a predetermined amount of impression material capable of being polymerized by subjection to visible actinic light, and an opaque cover sheet extending across said impression material and the edges of said cover being sealed at least to the rim of the walls of said tray to maintain said impression material unpolymerized until it is desired to impress dental anatomy into the impression material, whereby said tray and material therein comprises a merchandizable dental product.

9. The impression tray according to claim 8 in which the edges of said cover sheet are sealed to the rim of the tray by cement capable of permitting said cover sheet to be peeled from the rim of the tray to expose the impression material for use.

10. The impression tray according to claim 8 in which said opaque outer walls comprise light-reflecting sheet metal foil conformed to all exterior surfaces of said tray and having a rim portion adjacent the rim of said tray sealed to the edge of said cover.

11. The impression tray according to claim 10 in which said cover sheet comprises sheet metal foil and the rim portion of the conformed light-reflecting foil on said tray includes a peripheral flange peelably sealed relative to the peripheral edges of said cover sheet.

12. The impression tray according to claim 2 further characterized by said actinic light being of the visible light spectrum and limited substantially from about 360 to about 600 nanometers.

13. A method of forming a dental impression in polymerizable flowable impression material capable of being rendered permanently elastomeric to form a mold shape having a memory comprising the steps of;
  a. placing a predetermined quantity of said flowable material in a transparent impression tray having walls defining a recess,
  b. impressing said material in said tray against dental anatomy in an oral cavity of which a mold is desired,
  c. applying visible actinic light to the walls of said tray for a relatively short period of time adequate to effect polymerization of said material to form a permanent elastomeric mold having a memory, and
  d. reflecting said actinic light from surfaces of the walls of said tray directly into the body of impression material contained in said tray to insure thorough penetration of said material by said light.

14. The method according to claim 13 in which said actinic light is limited to a visible light spectrum of about 360 to about 600 nanometers.

15. The method according to claim 14 in which the period of time during which said actinic light of said nanometer range is applied to said tray does not exceed about two minutes.

* * * * *